United States Patent
Hawthorne et al.

(10) Patent No.: US 9,851,339 B2
(45) Date of Patent: *Dec. 26, 2017

(54) SAMPLING AN OIL COMPOSITION AND DETERMINING MINIMUM MISCIBILITY PRESSURE OF AN OIL COMPOSITION WITH A FLUID

(71) Applicant: Energy & Environmental Research Center Foundation, Grand Forks, ND (US)

(72) Inventors: Steven B. Hawthorne, Grand Forks, ND (US); David J. Miller, Grand Forks, ND (US)

(73) Assignee: Energy and Environmental Research Center Foundation, Grand Forks, ND (US)

( * ) Notice: Subject to any disclaimer, the term of this patent is extended or adjusted under 35 U.S.C. 154(b) by 17 days.

This patent is subject to a terminal disclaimer.

(21) Appl. No.: 14/825,351

(22) Filed: Aug. 13, 2015

(65) Prior Publication Data

US 2016/0047226 A1 Feb. 18, 2016

Related U.S. Application Data

(60) Provisional application No. 62/037,740, filed on Aug. 15, 2014.

(51) Int. Cl.
*E21B 47/06* (2012.01)
*G01N 33/28* (2006.01)

(52) U.S. Cl.
CPC ......... *G01N 33/2823* (2013.01); *E21B 47/06* (2013.01)

(58) Field of Classification Search
CPC ........... E21B 47/06; E21B 43/25; E21B 43/16
See application file for complete search history.

(56) References Cited

U.S. PATENT DOCUMENTS 4,455,860 A 6/1984 Cullick et al.
2006/0289157 A1 12/2006 Rao
(Continued)

FOREIGN PATENT DOCUMENTS

GB 2443077 B 3/2011
WO WO-2015/031341 A1 3/2015

OTHER PUBLICATIONS

"International Application Serial No. PCT/US2014/052674, International Preliminary Report on Patentability dated Mar. 10, 2016", 8 pgs.

(Continued)

*Primary Examiner* — Zakiya W Bates
(74) *Attorney, Agent, or Firm* — Schwegman Lundberg & Woessner, P.A.

(57) ABSTRACT

Various embodiments disclosed relate to methods and apparatuses for determining a minimum miscibility pressure of a fluid with and oil composition. In various embodiments, the method can include placing a fluid into a pressure chamber at a first pressure. The pressure chamber can include at least one capillary tube having one end disposed in an oil composition in the pressure chamber. The fluid can include at least one of a gas, a liquid, and a supercritical fluid. The method can include measuring a height of the oil composition in at least one of the capillary tubes. The method can include repeating the measuring for at least one cycle using a second pressure different than the first pressure. The method can include determining the minimum miscibility pressure of the oil composition with the fluid by extrapolating the pressure at a height of the oil in the at least one capillary tube of zero from the two or more measurements of the height of the oil composition in the at least one capillary tube.

15 Claims, 8 Drawing Sheets

(56) References Cited

U.S. PATENT DOCUMENTS

| | | |
|---|---|---|
| 2014/0232853 A1 | 8/2014 | Lewis |
| 2015/0059446 A1 | 3/2015 | Agar et al. |
| 2015/0060057 A1 | 3/2015 | Hawthorne et al. |
| 2015/0283541 A1 | 10/2015 | Curran et al. |
| 2016/0047791 A1 | 2/2016 | Miller et al. |

OTHER PUBLICATIONS

"International Application Serial No. PCT/US2014/052674, International Search Report dated Oct. 28, 2014", 3 pgs.

"International Application Serial No. PCT/US2014/052674, Written Opinion dated Oct. 28, 2014", 6 pgs.

Ayirala, Subhash C, "Measurement and Modeling of Fluid-Fluid Miscibility in Multicomponent Hydrocarbon Systems", A Dissertation Submitted to the Graduate Faculty of the Louisiana State University and Agricultural and Mechanical College in partial fulfillment of the Requirements for the degree of Doctor of Philosophy in The Department of Petroleum Engineering, (Aug. 2005), 205 pgs.

Rao, Dandina N., "A new technique of vanishing interfacial tension for miscibility determination", *Fluid Phase Equilibria*, 139(1-2), (1997), 311-324.

"U.S. Appl. No. 14/470,241, Non Final Office Action dated Nov. 28, 2016", 26 pgs.

"U.S. Appl. No. 14/470,241, Response filed Feb. 22, 2017 to Non Final Office Action dated Nov. 28, 2016", 12 pgs.

"Chinese Application Serial No. 201480047982.8, Office Action dated Aug. 18, 2016", W/ English Translation, 24 pgs.

"Chinese Application Serial No. 201480047982.8, Response filed Jan. 3, 2017 to Office Action dated Aug. 18, 2016", w/ English Claims, 11 pgs.

"Determination of Minimum Miscibility Pressure of Formation Oil and Carbon Dioxide in Daluhu Oilfield Fan Block 124", w/ English Abstract—Oil Gas Geology and Recovery Rate, vol. 9, No. 6, (Dec. 31, 2002), 4 pgs.

"European Application Serial No. 14771415.8, Response filed Nov. 18, 2016 to Communication pursuant to Rules 161(2) and 162 EPC dated May 9, 2016", 12 pgs.

Ping, Guo, et al., "Determination of Minimum Miscibility Pressure of Carbon Dioxide in Dagang Oilfield", w/ English Abstract Southwest College Journal, vol. 21, No. 3-19-21, (Aug. 31, 1999), 5 pgs.

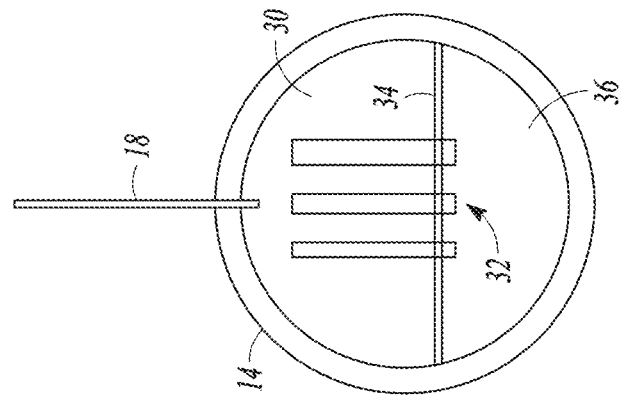
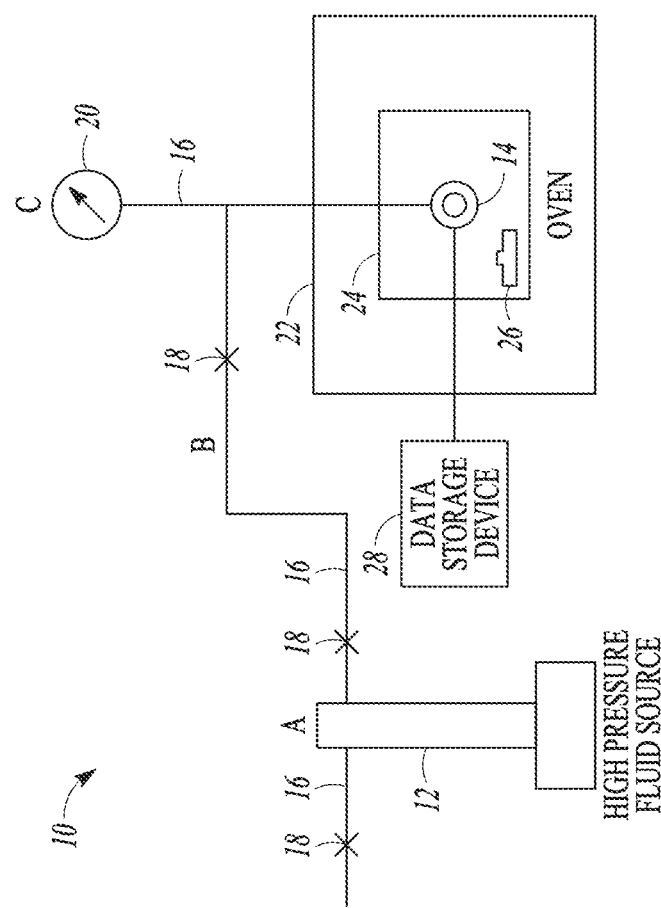
FIG. 1B
FIG. 1A

| | EXPERIMENTALLY MEASURED MMP (PSI) | | | | | |
|---|---|---|---|---|---|---|
| P CH4 | CAPILLARY 1 | CAPILLARY 2 | CAPILLARY 3 | MEAN MMP | SD | RSD |
| 0 | 1409 | 1453 | 1464 | 1442 | 29 | 2.0% |
| 0 | 1439 | 1428 | 1425 | 1431 | 7 | 0.5% |
| 101 | 1582 | 1603 | 1543 | 1576 | 30 | 1.9% |
| 111 | 1632 | 1685 | 1614 | 1644 | 37 | 2.2% |
| 205 | 1787 | 1756 | 1753 | 1765 | 19 | 1.1% |
| 306 | 1867 | 1815 | 1849 | 1844 | 26 | 1.4% |
| 400 | 1974 | 1969 | 1960 | 1968 | 7 | 0.4% |
| 500 | 2036 | 2058 | 2044 | 2046 | 11 | 0.5% |
| 601 | 2242 | 2284 | 2312 | 2279 | 36 | 1.6% |
| 704 | 2480 | 2493 | 2441 | 2471 | 27 | 1.1% |
| 698 | 2409 | 2435 | 2582 | 2475 | 93 | 3.8% |
| 850 | 2496 | 2528 | 2555 | 2526 | 30 | 1.2% |
| 1002 | 2648 | 2672 | 2722 | 2681 | 38 | 1.4% |
| 1005 | 2665 | 2655 | 2669 | 2663 | 7 | 0.3% |
| 1100 | 2878 | 2846 | 2858 | 2861 | 16 | 0.6% |
| 1208 | 2875 | 2877 | 2904 | 2885 | 16 | 0.6% |

FIG. 8

SAMPLING AN OIL COMPOSITION AND DETERMINING MINIMUM MISCIBILITY PRESSURE OF AN OIL COMPOSITION WITH A FLUID

CROSS-REFERENCE TO RELATED APPLICATION

This application claims the benefit of priority to U.S. Provisional Patent Application Ser. No. 62/037,740, filed Aug. 15, 2014, the disclosure of which is incorporated herein in its entirety by reference.

BACKGROUND OF THE INVENTION

Crude oil miscibility pressure with different fluids is an important parameter to optimize for enhanced oil recovery. The "minimum miscibility pressure," or "MMP," is an operating parameter that is useful for the successful operation of enhanced oil recovery processes such as the injection of fluids including, but not limited to, carbon dioxide, natural gas, and nitrogen into an oil reservoir. The injection of such fluids can increase production from the treated subterranean formation by at least one of swelling the crude oil, reducing oil viscosity, and forming a mobile phase including the injected fluid and oil components.

The most common available experimental techniques to determine fluid MMP in crude oil under reservoir conditions are slim-tube displacement and pressure—composition diagrams. Among these, the slim-tube technique is presently considered the "petroleum industry standard" to determine gas—oil miscibility. In this technique, miscibility is indirectly determined from oil recovery. However, there exists no standard design, standard operating procedure, and no standard set of criteria for determining MMP using slim-tube tests. Moreover, the slim-tube test's definition of miscibility as the break-over point in the oil recovery-versus-pressure curve requires several slow-rate slim-tube displacement tests, and hence, this technique is costly and time-consuming (4-5 weeks).

Two fluids can be defined as miscible at temperature and pressure conditions where the interfacial tension between the two fluids is zero. A vanishing interfacial tension (VIT) technique has been reported (Rao, Dandina N. *Fluid Phase Equilibria* 1997, 139(1), 311-324) that can determine fluid MMP in crude oil. In Rao's VIT method, the gas—oil interfacial tension is measured at reservoir temperature and at varying pressures or enrichment levels of the gas phase. The gas—oil miscibility conditions are then determined by extrapolating the plot of interfacial tension against pressure or enrichment to zero interfacial tension. However, the extrapolation in Rao's VIT technique is difficult since it is performed using a curve whose slope increases as it nears the axis with which the point of intersection must be determined. Additionally, Rao's VIT technique requires extremely accurate measurements of capillary tube inner diameter, and requires a tedious measurement of the density of each phase under each of the pressure and temperature conditions tested.

SUMMARY OF THE INVENTION

Various embodiments of the present invention provide a method of determining a minimum miscibility pressure of a fluid with an oil composition. The method includes placing a fluid into a pressure chamber at a first pressure. The pressure chamber includes at least one capillary tube having one end disposed in an oil composition in the pressure chamber. The fluid includes at least one of a gas, a liquid, and a supercritical fluid. The method includes measuring a height of the oil composition in at least one of the capillary tubes. The method includes repeating the measuring for at least one cycle using a second pressure different than the first pressure. The method also includes determining the minimum miscibility pressure of the oil composition with the fluid by extrapolating the pressure at a height of the oil in the at least one capillary tube of zero from the two or more measurements of the height of the oil composition in the at least one capillary tube.

Various embodiments of the present invention provide a method of determining a minimum miscibility pressure of a fluid with an oil composition. The method includes placing a fluid into a pressure chamber at a first pressure. The pressure chamber includes a plurality of capillary tubes each having one end disposed in an oil composition in the pressure chamber and each having a different inner diameter. The fluid includes at least one of a gas, a liquid, and a supercritical fluid. The fluid includes at least one of carbon dioxide, nitrogen, methane, ethane, propane, hydrogen sulfide, n-butane, iso-butane, natural gas, natural gas liquids, and produced gas. The oil composition includes crude oil, a crude oil fraction, a mixture substantially resembling crude oil, and a mixture substantially resembling a crude oil fraction. The method includes measuring a height of the oil composition in each of the capillary tubes. The method includes repeating the measuring for at least one cycle using a second pressure different than the first pressure. The method also includes determining the minimum miscibility pressure of the oil composition with the fluid by extrapolating the pressure at a height of the oil in the at least one capillary tube of zero independently for each of the capillary tubes from the two or more measurements of the height of the oil composition in each of the capillary tubes, and averaging the at least two extrapolated pressures.

Various embodiments of the present invention provide a method of sampling one or more components of an oil composition. The method includes placing a fluid into a pressure chamber at a first pressure. The pressure chamber includes an oil composition therein that contacts the fluid. The fluid includes at least one of a gas, a liquid, and a supercritical fluid. The method can include taking a sample of at least one of the fluid and the oil composition from the pressure chamber. In some embodiments, the method includes characterizing at least one aspect of the sample.

Various embodiments of the present invention provide an apparatus for sampling at least one component of an oil composition. The apparatus includes a pressure chamber configured to have oil composition therein The pressure chamber is configured to have a fluid including at least one of a gas, a liquid, and a supercritical fluid placed therein at a first pressure sufficient to contact the oil composition. The pressure chamber is configured such that a sample of at least one of the fluid and the oil composition can be taken at the first pressure.

Various embodiments of the present invention provide an apparatus for determining a minimum miscibility pressure of a fluid with an oil composition. The apparatus includes a pressure chamber including at least one capillary tube configured to have one end disposed in an oil composition in the pressure chamber. The pressure chamber is configured to have a fluid including at least one of a gas, a liquid, and a supercritical fluid placed therein at a first pressure. The pressure chamber is configured such that a height of the oil composition in at least one of the capillary tubes can be measured.

In various embodiments, the present invention provides certain advantages over other methods and apparatuses for determining minimum miscibility pressures of an oil composition and a fluid medium. For example, various embodiments of the method can be performed using simpler and less expensive instrumentation than other techniques for determining a fluid MMP in an oil composition. Various embodiments can be much faster and simpler to perform than other methods for determining a fluid MMP in an oil composition, such as slim-tube, rising-bubble, and Rao's VIT technique. The results achieved by various embodiments of the present method can be more consistent and less operator dependent than other techniques, such as the slim-tube technique.

Various embodiments of the method can accurately measure a fluid MMP in an oil composition without reaching the MMP pressure during the method, unlike the slim-tube method and Rao's VIT technique. Various embodiments of the method can measure a fluid MMP in an oil composition without performing a tedious step of measuring the density of the oil or fluid phase, unlike techniques such as Rao's VIT technique. In various embodiments, since the need to transfer both fluids to the densitometer is eliminated, a constant oil composition is assured during the experiments. Various embodiments of the method can be performed without knowing the diameter of the capillary tube used, unlike techniques such as Rao's VIT technique which requires knowledge of the inner diameter of the capillary tube. Various embodiments of the method can extrapolate a fluid MMP in an oil composition from a linear plot, unlike other techniques, resulting in greater speed and accuracy, and in less need for measurements at pressures near the MMP. Various embodiments of the method can be performed using a smaller total quantity of oil (e.g., a few grams or less), such as compared to Rao's VIT technique.

Various embodiments of the present method are at least one of simpler, quicker, and less expensive to perform than other MMP methods, allowing cost- and time-effective multiple MMP determinations, which allows investigating the effect of multiple parameters on MMP. For example, in various embodiments, MMP values can be tracked during the entire production of a reservoir, rather than relying on only the MMP value originally determined. In various embodiments, the fluid MMP in an oil composition as the oil composition or oil/gas ratio changes can efficiently be investigated by exposing produced oil to various fluid compositions, rather than relying only on predictive modeling correlations.

BRIEF DESCRIPTION OF THE FIGURES

The drawings illustrate generally, by way of example, but not by way of limitation, various embodiments discussed in the present document.

FIG. 1A illustrates an apparatus that can be used to perform the method, in accordance with various embodiments.

FIG. 1B illustrates an enlarged view of the high-pressure cell of an apparatus, in accordance with various embodiments.

FIG. 8 illustrates test results using the method and apparatus disclosed, in accordance with various embodiments.

DETAILED DESCRIPTION OF THE INVENTION

Figure 2:
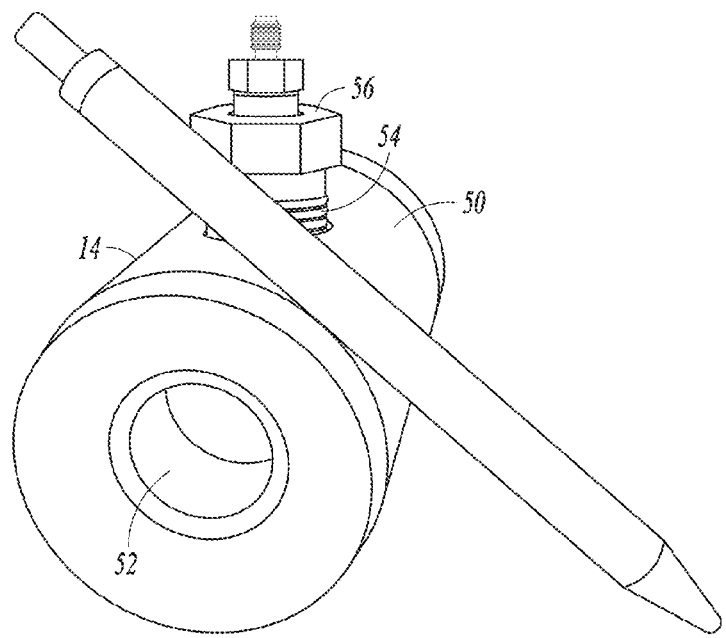
FIG. 2 is a photograph of the high-pressure cell of an apparatus during test conditions, in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods of manufacturing described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

As used herein, the term "subterranean material" or "subterranean formation" refers to any material under the surface of the earth, including under the surface of the bottom of the ocean. For example, a subterranean formation or material can be any section of a wellbore and any section of a subterranean petroleum- or water-producing formation or region in fluid contact with the wellbore. Placing a material in a subterranean formation can include contacting the material with any section of a wellbore or with any subterranean region in fluid contact therewith. Subterranean materials can include any materials placed into the wellbore such as cement, drill shafts, liners, tubing, or screens; placing a material in a subterranean formation can include contacting with such subterranean materials. In some examples, a subterranean formation or material can be any below-ground region that can produce liquid or gaseous petroleum materials, water, or any section below-ground in fluid contact therewith. For example, a subterranean formation or material can be at least one of an area desired to be fractured, a fracture or an area surrounding a fracture, and a flow pathway or an area surrounding a flow pathway, wherein a fracture or a flow pathway can be optionally fluidly connected to a subterranean petroleum- or water-producing region, directly or through one or more fractures or flow pathways.

The term "downhole" as used herein refers to under the surface of the earth, such as a location within or fluidly connected to a wellbore.

The term "fluid" as used herein can refer to a liquid, a gas, a supercritical fluid, or any suitable combination thereof.

The term "flooding" as used herein with regard to treatment of subterranean formations refers to miscible flooding, a process that includes injecting a fluid to aid in the mobility of at least a portion of petroleum materials in the subterranean formation.

Crude oil miscibility pressure with different fluids is an important parameter to optimize enhanced oil recovery. Two fluids can be defined as miscible at temperature conditions and pressure conditions where the interfacial tension between the fluids is zero. However, generally, crude oil is found as a mixture of a wide variety of hydrocarbons, each having a different molecular weight. If each of the components of crude oil were purified and individually tested for MMP with a fluid, a variety of different MMPs would be found, with generally lower MMPs for lower molecular weight materials and generally higher MMPs for higher molecular weight materials. As the pressure of a fluid with an oil composition that includes a mixture of materials is increased, a portion of the oil composition that can be predominantly the lowest molecular weight portions of the oil composition can become miscible with or substantially soluble in the fluid first (e.g., those components of the oil composition having an MMP, if MMP was measured for the purified components, that is at or lower than the pressure of the fluid), while another portion oil the oil composition that can be predominantly the higher molecular weight components can remain immiscible with or insoluble with the fluid (e.g., those components of the oil composition having an MMP, if MMP was measured for the purified component, that is higher than the pressure of the fluid). As the pressure is increased, a greater proportion of the oil composition becomes miscible with or substantially soluble in the fluid, such as the higher molecular weight species in the oil composition. In various embodiments, for oil compositions including a mixture of species having a range of at least one of molecular weights, structures, and properties, and a corresponding range of pressures over which various proportions of the oil composition are miscible with a given fluid due to different individual MMPs for various component of the oil composition (if measured in a purified state), the MMP can be defined as the minimum pressure wherein about 50 wt % of the oil composition is miscible with (e.g., experiences zero interfacial tension with) or is solubilized in the fluid (e.g., is substantially in the fluid phase and is substantially not in the oil composition phase), or wherein about 40 wt % to about 60 wt %, about 30 wt % to about 70 wt %, or about 1 wt % or less, or about 2 wt %, 3, 4, 5, 6, 7, 8, 9, 10, 12, 14, 15, 20, 25, 30, 35, 40, 45, 50, 55, 60, 65, 70, 75, 80, 85, 90, 95, 96, 97, 98, or about 99 wt % or more of the oil composition becomes miscible with or is solubilized in the fluid.

In various embodiments, the present invention provides a method of determining a minimum miscibility pressure of a fluid with an oil composition. The fluid can be any suitable fluid, such as a gas, a liquid, a supercritical fluid, or any suitable combination thereof. The gas, liquid, or supercritical fluid can be any suitable one or more materials, such as at least one of carbon dioxide, nitrogen, methane, ethane, propane, hydrogen sulfide, n-butane, iso-butane, natural gas, natural gas liquids, and produced gas (e.g., gas produced by a subterranean formation). The oil composition can be any suitable oil composition, whether synthetic or naturally derived. The oil composition can be crude oil, or a crude oil fraction (e.g., a portion of a crude oil fraction that has been distilled or otherwise separated from the crude oil). The oil composition can be a sample that resembles (e.g., has a composition substantially similar to) crude oil or a crude oil fraction. The oil composition can be a live oil sample, for example, a crude oil sample taken from a subterranean formation, such as a crude oil sample that is maintained at the conditions of the subterranean formation from which it was taken (e.g., pressure, temperature, or a combination thereof).

The method can include placing the fluid into a pressure chamber. The pressure chamber can be any suitable pressure chamber that can maintain a pressure. In some embodiments, the pressure chamber is encompassed by a temperature controlled environment, such as an oven, such that the temperature of the pressure chamber can be precisely controlled. The temperature used during each height measurement can be approximately a temperature of a subterranean formation, such as the formation wherein a flooding treatment is desired to be performed using a fluid having a substantially similar composition to the fluid tested. Although MMP can vary significantly for different temperatures at a given pressure, the density of various fluids, such as $CO_2$, can vary less for the different temperatures at the given pressure. The pressure chamber can include a sample of the oil composition therein. The pressure chamber includes at least one capillary tube therein, wherein one end of the capillary tube is disposed in the oil composition in the pressure chamber, and wherein the other end of the capillary tube is disposed in the fluid composition in the pressure chamber. The oil composition is generally located on the bottom of the pressure chamber, and the fluid is generally located on the top of the pressure chamber, with interfacial tension separating the fluid and the oil composition.

The capillary tube can be any suitable capillary tube. The capillary tube can have any suitable diameter. The capillary tube can have any suitable shape, such as straight, curved, or having angular bends therein. The capillary tube can be clear (e.g., transparent or translucent), such that the contents can be observed visually. The capillary tube can be opaque if a non-visual method of determining a height of the oil composition therein is used. The capillary tube can be any suitable material, such as glass or plastic. The pressure chamber includes at least one capillary tube, but any number of capillary tubes can be included therein, such as 2, 3, 4, 5, 6, 7, 8, 9, 10, 12, 14, 16, 18, 20, 30, 40, 50, 75, or 100 or more capillary tubes. The capillary tubes can have the same inner diameter. The capillary tubes can have different inner diameters. Any suitable inner diameter can be used, such about 0.001 mm to about 5 mm, or about 0.001 mm or less, or about 0.005 mm, 0.01, 0.05, 0.1, 0.5, 1, 1.5, 2, 2.5, 3, 3.5, 4, 4.5, or about 5 mm or more.

The pressure chamber can be any suitable size, such that it can include the capillary tubes, the oil composition, and the fluid. The oil composition sample can be any suitable size, and the fluid that enters the pressure chamber can be any suitable quantity. The apparatus, including the pressure chamber, can be scaled up or down without limitation. In some embodiments, the method can include cleaning the pressure chamber prior to placing the oil composition and the fluid therein. In some embodiments, the method can include evacuating other gases from the pressure chamber prior to placing the oil composition and the fluid therein. The evacuating can be performed in any suitable way. For example, prior to adding the oil composition to the pressure chamber, the fluid can be added to the pressure chamber and allowed to flow therethrough such that contaminating materials are flushed out, or a vacuum can be applied to the pressure chamber and the fluid can be allowed to flow in to relieve the vacuum (for one or more cycles). In various embodiments, the accuracy of the method can be improved by cleaning the pressure chamber and by removing atmospheric gases or other gases from the pressure chamber prior to adding the fluid and the oil composition thereto.

The method can include placing the fluid into the pressure chamber at a first pressure. The first pressure can be any suitable pressure in the pressure chamber, wherein the first pressure is lower than the MMP of the fluid and the oil composition (e.g., wherein less than 50 wt % of the oil composition experiences zero interfacial pressure with the fluid). The first pressure can be similar to a downhole pressure, such as a pressure wherein the oil composition was obtained. The first pressure can be achieved by any suitable means. For example, the fluid can flow to the pressure chamber from a pressurized source, and a valve between the pressurized source and the pressure chamber can be opened to raise the pressure. In some embodiments, the pressure, temperature, or both, of the fluid and the oil composition is allowed to equilibrate. Any suitable degree of equilibration can be performed. The equilibration can include allowing the system to stabilize for about 0.1 second to about 4 hours, or about 0.1 second or less, or about 1 second, 5 seconds, 10 seconds, 20 seconds, 30 seconds, 45 seconds, 1 minutes, 2 minutes, 3 minutes, 4 minutes, 5 minutes, 10 minutes, 20 minutes, 30 minutes, 45 minutes, 60 minutes, 2 hours, 3 hours, or about 4 hours or more, wherein during the stabilization, the oil composition and the fluid can obtain at least one or a more even pressure and temperature, and the oil composition and fluid can partition such that none of the oil composition is stably miscible with the fluid or such that some proportion of the oil composition becomes stably miscible with the fluid.

With the fluid and the oil composition in the pressure chamber at the first pressure, the method can include measuring the height of the oil composition in the at least one capillary tubes. The height of the oil composition in at least one of the capillary tubes can be the distance between the surface of the oil composition in the pressure chamber and the surface of the oil composition in the capillary tube. In embodiments including multiple capillary tubes in one or more pressure chambers, the method can include measuring the height of the oil composition in more than one of the capillary tubes, such as in each of the capillary tubes.

The method can include repeating the measuring for at least one cycle using a second pressure in the pressure chamber different than the first pressure. The second pressure can be any suitable pressure in the pressure chamber, wherein the second pressure is lower than the MMP of the fluid and the oil composition (e.g., wherein less than 50 wt % of the oil composition experiences zero interfacial pressure with the fluid). The second pressure can be similar to a downhole pressure, such as a pressure wherein the oil composition was obtained. The second pressure can be achieved by any suitable means, such as in a similar manner as the first pressure is achieved. The repeating of the cycle of setting a pressure and measuring the height of the oil composition in the oil or more capillary tubes can be repeated for any suitable number of times, wherein a greater number of repeated measurements generally results in greater accuracy of the MMP determination, such as 2 times, 3, 4, 5, 6, 7, 8, 9, 10, 12, 14, 16, 18, 20, 22, 24, 26, 28, 30, 35, 40, 45, 50, 55, 60, 65, 70, 75, 80, 85, 90, 100, 125, 150, 175, 200, 250, 500, 750, or about 1,000 or more times. For each repeated cycle, the pressure can be different or the same as another pressure tested; however, at least two different pressures are tested for a given inner diameter of capillary so that the extrapolation of MMP can be performed. In some embodiments, the first or second pressure can be predetermined. In some embodiments, the method can include recording at least one of the height, the pressure, and the temperature.

In some embodiments, repeating the measuring for at least one cycle can be performed in the same pressure chamber, using the same fluid and the same oil composition, by simply changing the pressure of the fluid to the second pressure and observing the new height of the oil composition in the at least one capillary tube. In other embodiments, the repeating can be done by removing the oil composition or the fluid, and by replacing the oil composition and the fluid and achieving the second pressure, e.g., the method does not require that the height of the oil composition at the first and second pressure be determined proximate in time or even using the same fluid and oil composition, so long as the fluid and oil composition used for the height measurement at the second pressure have approximately the same composition as the fluid and oil composition used for the height measurement at the first pressure, and so long as the capillary tube used for the height measurement at the second pressure has about the same inner diameter as the capillary tube used for the height measurement at the first pressure.

The height measurements can be performed in the same pressure chamber, different pressure chambers, and with small or large time separation between measurements. In some embodiments, multiple pressure chambers can be used, each having a substantially similar fluid, oil composition, and capillary tube therein, and the first and second height measurements can be taken substantially simultaneously. In some embodiments, multiple pressure chambers can be used, each having a substantially similar fluid and oil composition therein, but each having a capillary tube with a different inner diameter therein, and the first and second height measurements can be taken independently for each capillary tube. In some embodiments, a single pressure chamber can be used, having multiple capillary tubes therein, at least two of which having different inner diameters, and multiple height measurements (e.g., one for each capillary) can be taken from within a single pressure chamber at each pressure.

The method can include determining the MMP of the oil composition with the fluid by extrapolating the pressure at a height of the oil in the at least one capillary tube of zero from the two or more measurements of the height of the oil composition in the at least one capillary tube. In embodiments having multiple capillary tubes having different inner diameters, the MMP can be extrapolated for each capillary tube (e.g., for each inner diameter). In some embodiments, the MMP determined using each capillary tube (e.g., for each inner diameter) can be averaged to determine a single MMP.

In various embodiments, the method can be used to determine the MMP of certain portions or one or more certain components of the oil composition, as measured in a substantially purified state. Differences in MMP between components caused by, for example, at least one of molecular weight differences, differences in polarity, and differences in structure, can allow the method to selectively determine the MMP for one or more specific compounds of the oil composition, as measured in a substantially purified state. For example, the majority of height measurements can be taken using pressures that allow the particular portion or component of the oil composition for which MMP is desired to be measured to remain substantially immiscible with or substantially insoluble in the fluid (e.g., to substantially remain with the oil composition in the bottom of the pressure chamber, and predominantly not move to the upper portion of the pressure chamber with the fluid), but that cause that majority of the other fractions (e.g. lighter fractions) of the oil composition to be miscible with or substantially soluble in the fluid. As higher pressures are used, other portions or components (e.g., lower molecular weight fractions) can become miscible with or substantially soluble in the fluid, and the extrapolation of height measurements to the pressure at zero height can reflect the MMP of the remaining portions of the oil (e.g., the lightest molecular weight fractions that still remain immiscible with or substantially insoluble in the fluid at the pressures used). In some embodiments, the highest molecular weight fractions of the oil composition can have the highest MMPs, which can be measured by measuring the heights using pressures wherein the majority of the lower molecular weight fractions are miscible with the fluid.

In various embodiments, the oil composition includes a plurality of compounds having different MMPs with the fluid (e.g., if measured in a purified state), and the method includes selecting a first and second pressure such that a majority of a desired one or more compounds of the oil composition remains immiscible with or substantially insoluble in the fluid at both selected pressures, such that the determined MMP is approximately the MMP of the one or more compounds remaining immiscible with the fluid, or is approximately the MMP of the one or more compounds remaining immiscible with or substantially insoluble in the fluid that have the lowest MMP. In various embodiments, the oil composition includes a plurality of compounds having different MMPs with the fluid (e.g., if measured in a purified state), and the method includes selecting the first and second pressure such that each cause about 5-99 wt % (e.g., about 10 wt % to about 99 wt %, about 25 wt % to about 99 wt %, about 50 wt % to about 99 wt %, about 75 wt % to about 99 wt %, or about 5 wt % or less, or about 10 wt %, 15, 20, 25, 30, 35, 40, 45, 50, 55, 60, 65, 70, 75, 80, 85, 90, 95, 96, 97, 98, or about 99 wt % or more) of the oil composition to become miscible with or substantially soluble in the fluid, such that the determined MMP is approximately the MMP of one or more desired components of the oil composition, such as the MMP of the one or more desired components that remain substantially immiscible with or substantially insoluble in the fluid at the first and second pressure, or the MMP of the one or more desired components that remain substantially immiscible with or substantially insoluble in the fluid at the first and second pressure and that have about the lowest MMP of the components that remain immiscible with or substantially insoluble in the fluid at the first and second pressure. In various embodiments, the oil composition includes a plurality of compounds having different MMPs with the fluid (e.g., if measured in a purified state), and the method includes selecting the first and second pressure such that each cause no more than 0-95 wt % (e.g., about 0 wt % to 90 wt %, about 0 wt % to about 75 wt %, about 0 wt % to about 50 wt %, about 0 wt % to about 25 wt %, or about 0 wt % or less, or about 1 wt %, 2, 3, 4, 5, 6, 7, 8, 9, 10, 15, 20, 25, 30, 35, 40, 45, 50, 55, 60, 65, 70, 75, 80, 85, 90, or about 95 wt % or more) of the oil composition to become miscible with or substantially soluble in the fluid, such that the determined MMP is approximately the MMP of one or more desired components of the oil composition, such as the MMP of the one or more desired components that remain substantially immiscible with or substantially insoluble in the fluid at the first and second pressure, or the MMP of the one or more desired components that remain substantially immiscible with or substantially insoluble in the fluid at the first and second pressure and that have about the lowest MMP of the components that remain immiscible with or substantially insoluble in the fluid at the first and second pressure.

In some embodiments, the lower molecular weight components of an oil composition can have lower MMPs if measured in a purified state, and the higher molecular weight components of an oil composition can have higher MMPs if measured in a purified state. In various embodiments, the oil composition includes a plurality of compounds each having a different molecular weight, and the method includes selecting a first and second pressure such that a majority of a desired molecular weight fraction of the oil composition remains immiscible with or substantially insoluble in the fluid, such that the determined MMP is approximately the MMP of the desired molecular weight fraction, such as the MMP of the lowest molecular weight fraction of the higher molecular weight fractions remaining immiscible with or substantially insoluble in the fluid at the first and second pressure. In various embodiments, the oil composition includes a plurality of compounds each having a different molecular weight, and the method includes selecting the first and second pressure such that each cause about 5-99 wt % (e.g., about 10 wt % to about 99 wt %, about 25 wt % to about 99 wt %, about 50 wt % to about 99 wt %, about 75 wt % to about 99 wt %, or about 5 wt % or less, or about 10 wt %, 15, 20, 25, 30, 35, 40, 45, 50, 55, 60, 65, 70, 75, 80, 85, 90, 95, 96, 97, 98, or about 99 wt % or more) of the oil composition to become miscible with or substantially soluble in the fluid, such that the determined MMP is approximately the MMP of higher molecular weight fractions of the oil composition, such as the MMP of the lowest molecular weight fraction of the higher molecular weight fractions remaining immiscible with or substantially insoluble in the fluid at the first and second pressure. In various embodiments, the oil composition includes a plurality of compounds each having a different molecular weight, and the method includes selecting the first and second pressure such that each cause no more than 0-95 wt % (e.g., about 0 wt % to 90 wt %, about 0 wt % to about 75 wt %, about 0 wt % to about 50 wt %, about 0 wt % to about 25 wt %, or about 0 wt % or less, or about 1 wt %, 2, 3, 4, 5, 6, 7, 8, 9, 10, 15, 20, 25, 30, 35, 40, 45, 50, 55, 60, 65, 70, 75, 80, 85, 90, or about 95 wt % or more) of the oil composition to become miscible with or substantially soluble in the fluid, such that the determined MMP is approximately the MMP of lower molecular weight fractions of the oil composition, such as the MMP of the lowest molecular weight fraction of the higher molecular weight fractions remaining immiscible with or substantially insoluble in the fluid at the first and second pressure.

Various embodiments of the method including performing a flooding treatment of a subterranean formation in combination with the method of determining the MMP of a fluid and an oil composition. For example, the method can include performing a flooding treatment of a subterranean formation including therein a petroleum composition that is the same as or that substantially resembles the oil composition, wherein the flooding treatment is performed using the fluid at a pressure that is about equal to or above the determined MMP. In some embodiments, the method includes performing the method of determining the MMP using as the oil composition a sample produced from the subterranean formation after the flooding treatment has begun.

Various embodiments of the present invention provide an apparatus for determining the MMP of a fluid and an oil composition. The apparatus can be any suitable apparatus that can be used to carry out any embodiment of the method described herein.

The apparatus can include a pressure chamber including at least one capillary tube having one end configured to be disposed in an oil composition therein. The pressure chamber can be configured to have a fluid including at least one of a gas, a liquid, and a supercritical fluid placed therein at a first pressure. The pressure chamber can be configured such that a height of the oil composition in at least one of the capillary tubes can be measured. The pressure chamber can be configured to have the fluid placed therein at the first pressure and at a second pressure, wherein the pressure chamber is configured such that the height of the oil composition in at least one of the capillary tubes can be measured, such that the MMP of the oil composition with the fluid can be determined by extrapolating the pressure at a height of the oil in the at least one capillary tube of zero from the two or more measurements of the height of the oil composition in the at least one capillary tube.

In some embodiments, the pressure chamber includes at least two capillary tubes each having a different inner diameter. The apparatus can include a holder that holds the at least one capillary tube. The apparatus can include a recorder that is configured to record a pressure of the fluid and the corresponding height of the oil composition in at least one of the capillary tubes.

Various embodiments of the present invention provide a method of sampling one or more components of an oil composition. The method includes placing a fluid into a pressure chamber at a first pressure, wherein the first pressure in the sampling method can be any pressure, whether greater than, the same as, or lower than the MMP. The fluid includes at least one of a gas, a liquid, and a supercritical fluid. The fluid can be any suitable fluid described herein. The pressure chamber can be any suitable pressure chamber as described herein; however, the pressure chamber need not include capillary tubes. In some embodiments, the pressure chamber includes the capillary tubes, while in other embodiments the pressure chamber is free of capillary tubes. The pressure chamber can include a viewing window, or the pressure chamber can be free of a viewing window. The pressure chamber includes an oil composition therein that contacts the fluid. The oil composition is any suitable oil composition as described herein, such as an oil composition having multiple components, wherein one or more of the multiple components have different MMPs with the fluid if measured with the component in a substantially purified state. The method can include taking a sample of at least one of the fluid and the oil composition from the pressure chamber. The sample of the fluid can include any portions of the oil composition that are miscible with the fluid at the first pressure and at the temperature conditions used. The sample of the oil composition can include any portions of the oil composition that are immiscible with the fluid at the first pressure and at the temperature conditions used. In some embodiments, the sample is collected with a needle inserted into the pressure chamber. Any aspect of an embodiment of the method of determining MMP can be incorporated into various embodiments of the method sampling one or more components of the oil composition.

Visual observations have shown that crude oil hydrocarbons are mobilized into the upper (mobile) phase of an injected fluid including but not limited to $CO_2$ and natural gas. Contrary to conventional wisdom that says the MMP must be exceeded before significant hydrocarbon mobilization occurs, high pressure view cells show clearly that significant amounts of oil hydrocarbons can be mobilized into the upper injected fluid phase at pressures substantially below MMP, and that increasing amounts of hydrocarbon continue to be mobilized as pressure is increased to, and then above the MMP. Similarly, large amounts of oil hydrocarbons can precipitate from the upper mobile phase back into the lower bulk oil phase as the pressure is dropped from above MMP to a lower value (but still above MMP). As the pressure of the injected fluid is further dropped below MMP, large amounts of oil can continue to be lost from the upper mobile phase. These results, combined with the common observation that $CO_2$ enhanced oil recovery (EOR) floods can produce lighter crudes than the original oil demonstrate a need to determine the mobilized hydrocarbon composition (including both the mass of oil mobilized and its molecular weight distribution) in samples collected at both pressures and temperatures representative of EOR reservoir conditions.

In various embodiments, the present invention provides an apparatus and method that allows a sample to be collected at any position in a high-pressure view cell, e.g., to collect a sample of hydrocarbons either in the upper mobile phase or lower bulk oil phase, or in any additional extract phases of mixed injected fluid and oil hydrocarbons that may form ion the view cell. Samples of hydrocarbon can be collected from any position in the high-pressure view cell without disturbing either the pressure or temperature of the device, thus ensuring that the collected hydrocarbons accurately represent the hydrocarbon composition under the EOR conditions being simulated in the high pressure cell. The samples can be collected in a manner that allows for hydrocarbon analysis by conventional gas chromatography techniques. The apparatus and method have been used successfully to collect samples of mobilized oil hydrocarbons at pressures below, at, and above MMP, and at various temperatures representing reservoir conditions ranging from conventional shallower (cooler) reservoirs to deep (hotter) unconventional reservoirs, and has shown that large changes in the both the quantity of hydrocarbon and the molecular weight distribution of mobilized hydrocarbons varies dramatically as pressure of the injected fluid is varied from below, to, and above MMP. The method can be useful in better understanding and designing EOR floods.

In some embodiments, the method includes characterizing at least one aspect of the sample. For example, the method can include performing mass spectrometry, nuclear magnetic resonance spectroscopy, or infrared spectrometry on the sample to elucidate various aspects of the structures properties or characteristics. The method can provide a simple way to characterize the components of an oil composition that are miscible or immiscible with the fluid at various temperatures and pressures, and can be used to determine which fluids and which pressures should be used in a subterranean treatment to recover desired components of the oil composition, such as by selecting a pressure and fluid composition which will substantially cause one or more desired components of the oil composition to be miscible in the fluid.

Various embodiments of the present invention provide an apparatus for sampling at least one component of an oil composition. The apparatus includes a pressure chamber configured to have oil composition therein. The pressure chamber is configured to have a fluid including at least one of a gas, a liquid, and a supercritical fluid placed therein at a first pressure sufficient to contact the oil composition. The pressure chamber is configured such that a sample of at least one of the fluid and the oil composition can be taken at the first pressure.

Referring to FIG. 1(A), an apparatus 10 that can be used to perform the present method is illustrated. The apparatus 10 can include any readily available high-pressure fluid source 12, such as a commercially available high-pressure pump or gas cylinder capable of providing a range of pressures of the test fluid to a suitable commercially available high-pressure cell 14 under predetermined controlled conditions. The apparatus 10 can include suitable commercial tubing 16 and associated suitable commercially available high-pressure valves 18 used to control the flow of fluid into the high-pressure cell 14, a suitable commercially available pressure measurement device 20 to accurately measure pressure in the high-pressure test cell 14, and a suitable commercially available air-circulating oven 20 capable of accurate temperature control, of sufficient volume to accommodate the high-pressure cell 14 including a suitable commercially available high-temperature and pressure window 24 for viewing the high-pressure cell 14 during tests, a suitable commercially available video camera 26, and a suitable commercially available data storage device 28 for recording the pressure within and temperature of the high-pressure cell 14.

Referring to FIG. 1(B), an embodiment of a high-pressure cell 14 is illustrated having a high-pressure view cell window 30 and a plurality of suitable capillary glass tubes 32, each capillary glass tube 32 held in a suitable device 34 to hold them upright with the bottom of each tube open to a pool of oil 36 located at the bottom of the high-pressure cell 14.

Referring to FIG. 2, the high-pressure cell 14 that can be used to determine crude oil miscibility pressures with gas, liquid, and supercritical fluids is shown. The high-pressure cell 14 is shown in reference to a commercially available ball point pen resting on the surface of the high-pressure cell 14 to illustrate the size of the high-pressure cell 14. The high-pressure cell 14 includes an elongated cylindrical member 50 having a bore 52 therethrough, a bore 54 in the sidewall of the member 50 for receiving a suitable threaded member 56 or plurality of members 56 to attach one or more fluid lines 16 to the member 50. The member 50 may be constructed of any suitable material for use at the pressure levels and temperatures during testing.

Figure 3:
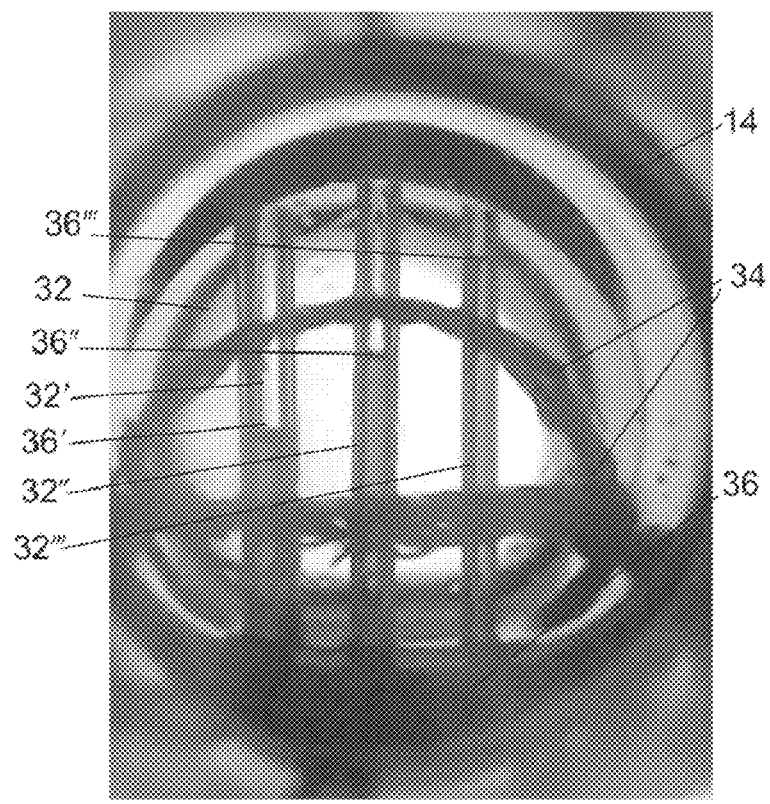
FIG. 3 is a photograph of the high-pressure cell 14 having a plurality of capillary tubes 32 located therein, in accordance with various embodiments.

Referring to FIG. 3, the high-pressure cell 14 is shown in a photograph having a plurality of capillary tubes 32 located therein. Each capillary tube 32 can be held within position in the high-pressure cell 14 by a suitable device 34. Each capillary tube 32 has one end thereof in a pool of oil 36 during a portion of the method of determining crude oil miscibility pressures with gas, liquid, and supercritical fluids at a predetermined pressure level and temperature level within the high-pressure cell 14. As shown, the high-pressure cell 14 can include a capillary tube 32' having an internal diameter larger than the internal diameter of either capillary tube 32" or capillary tube 32'''. Capillary tube 32" has an internal diameter smaller than the internal diameter of capillary tube 32' and an internal diameter larger than capillary tube 32'''. Capillary tube 32''' has an internal diameter smaller than either capillary tube 32" or capillary tube 32'. As shown during the method of determining crude oil miscibility pressures with gas, liquid, and supercritical fluids, the level of oil 36' in capillary tube 32' is at a level lower than the level 32" of capillary tube 32" and capillary tube 32'''. The level of the oil 36" of capillary tube 32" is greater than the level 36' of capillary tube 32' and less than the level of oil 36''' of capillary tube 32'''. The level of oil 36''' of capillary tube 32''' is higher than the level of oil 36" of capillary tube 32' and the level of oil 36' of capillary tube 32'. Under the predetermined pressure level and temperature level within the high-pressure cell 14, the pressure within the high-pressure cell 14, the temperature within the high-pressure cell 14, and the level of oil within each capillary tube 32', 32", and 32''' can be recorded by the data storage device 28 shown in FIGS. 1A and 1B. Although three capillary tubes have been illustrated, any number may be used in the method and apparatus disclosed herein, such as 1, 2, 3, 4, 5, or any plurality of capillary tubes.

Figure 4:
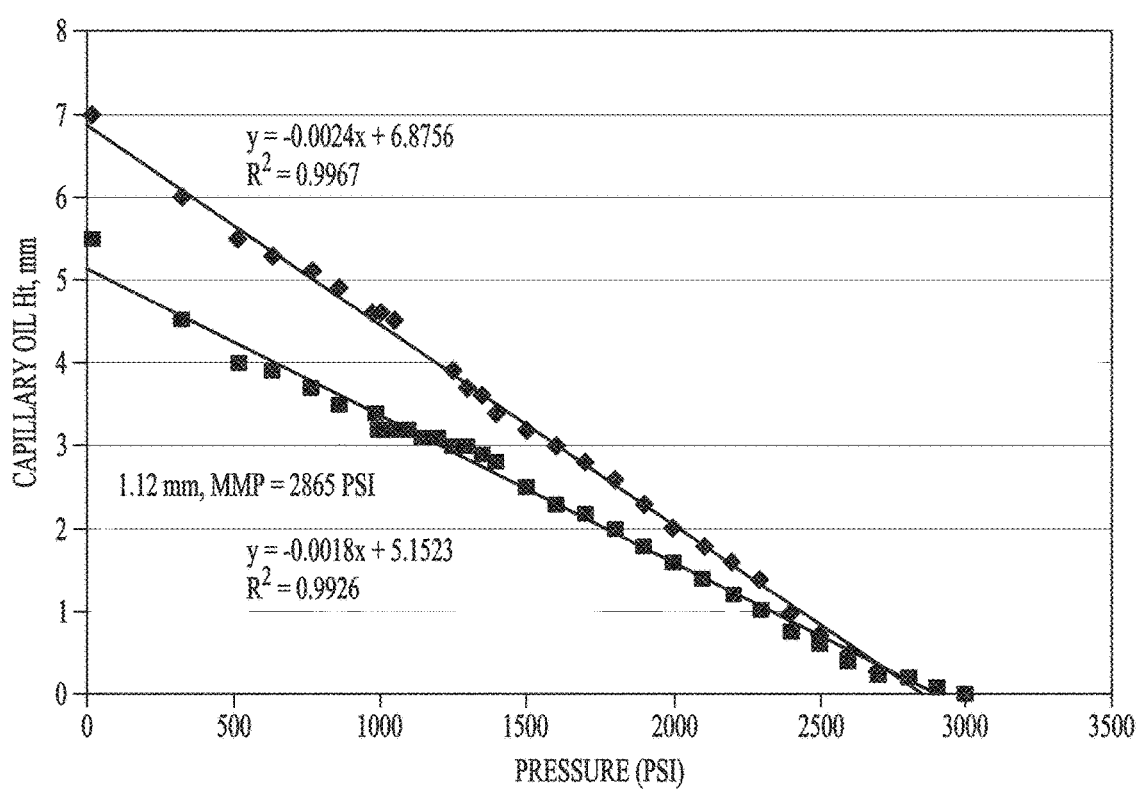
FIG. 4 illustrates an example of the plots for a test of the MMP for carbon dioxide injected into crude oil using the method and apparatus disclosed herein, in accordance with various embodiments.
Figure 5:
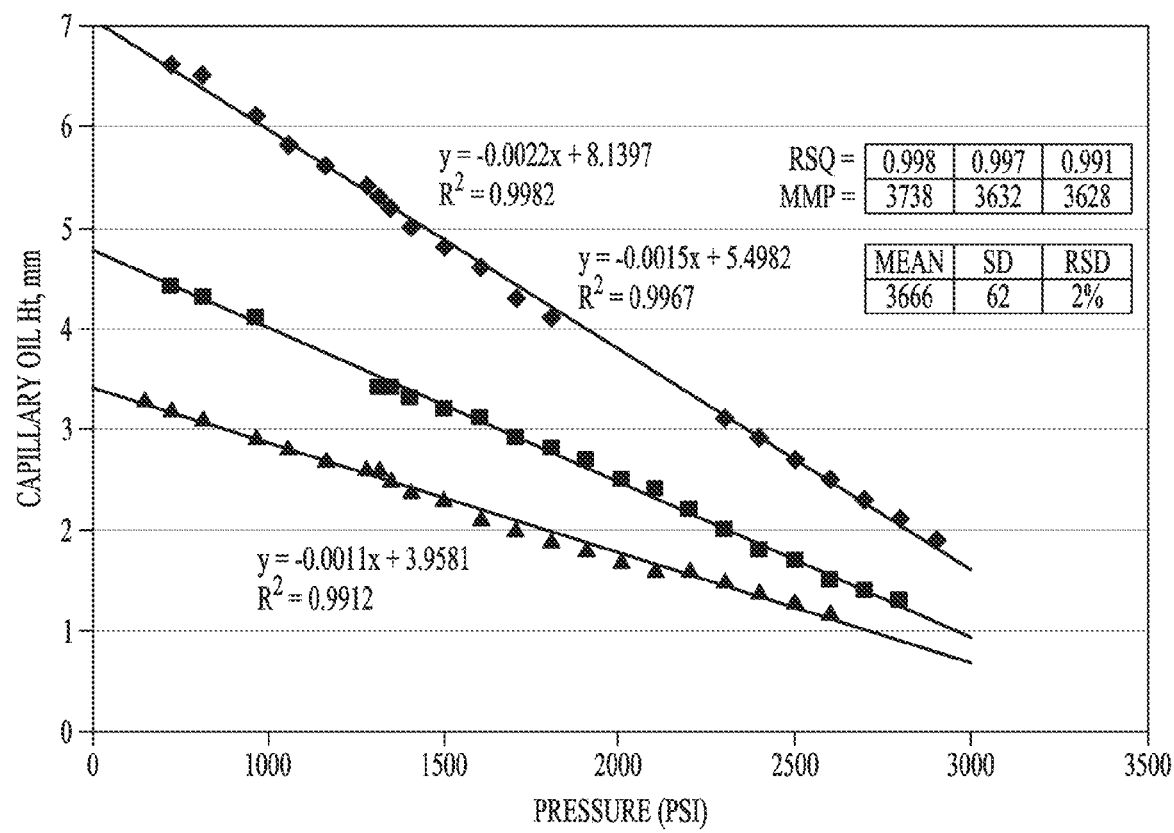
FIG. 5 illustrates an example of the plots for a test of the MMP for carbon dioxide injected into crude oil using the method and apparatus disclosed herein, in accordance with various embodiments.

The apparatus 10 can be operated by sequentially increasing the pressure of the gaseous fluid injected through line 16 into the high-pressure cell 14, allowing the injected gaseous fluid and oil to come to equilibrium within the high-pressure cell 14, and measuring the height or level 32', 32", 32''' of the oil in each capillary tube 32', 32", 32''' above the pool oil 36 at the bottom of the high-pressure cell 14. The measured heights or levels of oil can then be plotted versus the test pressures, and the resultant plots can be extrapolated to the pressure at which the oil height or level 32', 32", 32''' in the capillary tubes 32', 32", 32''' goes to zero, which is the desired MMP value for the particular test. Examples of the plots for a test of the MMP for carbon dioxide injected into crude oil are illustrated in FIGS. 4 and 5.

Figure 6:
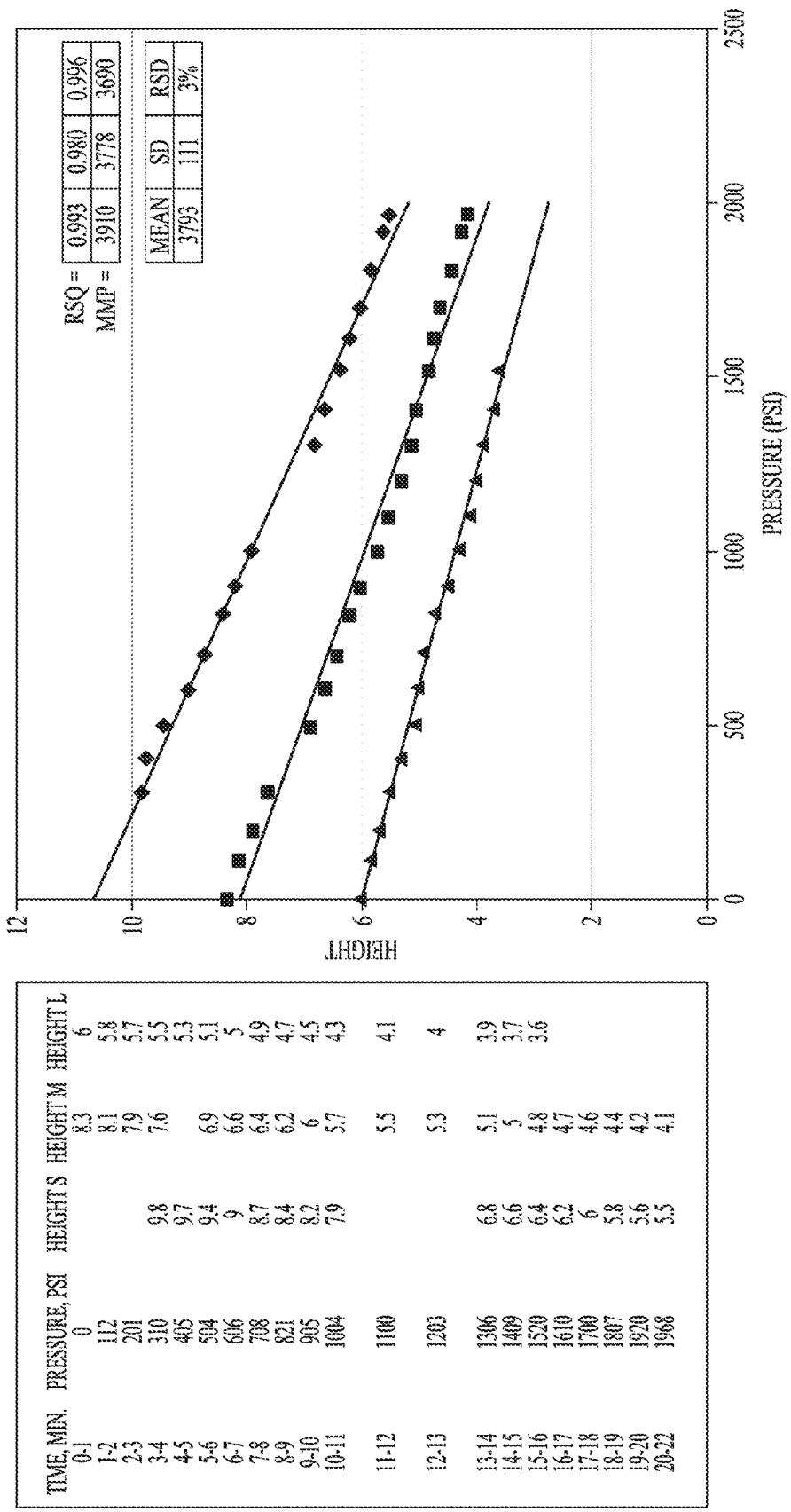
FIG. 6 illustrates the capillary height versus injection pressure to determine MMP values for a crude oil with pure methane, in accordance with various embodiments.
Figure 7:
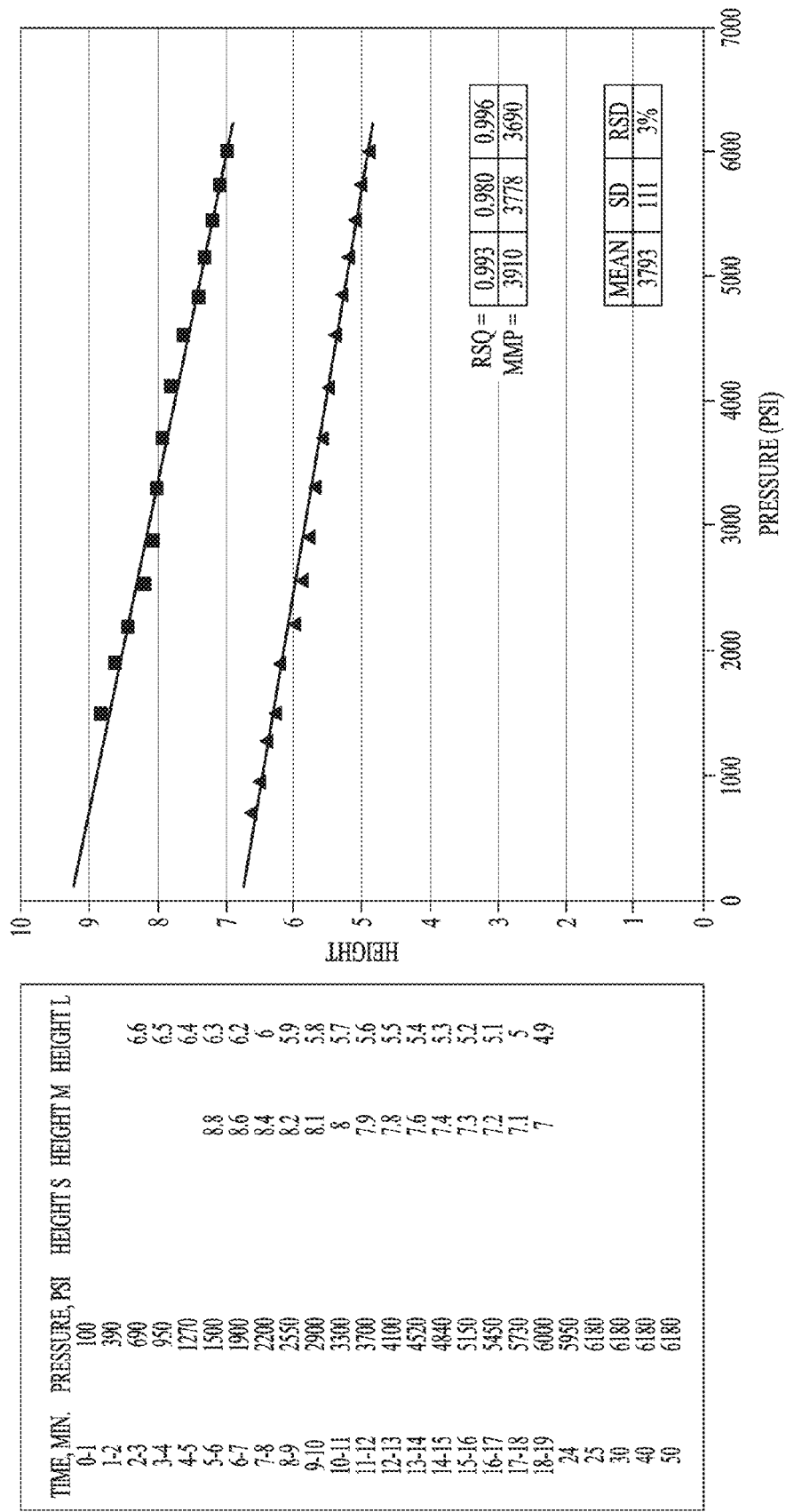
FIG. 7 illustrates the capillary height versus injection pressure to determine MMP values for pure nitrogen, in accordance with various embodiments.

The method and apparatus disclosed herein is capable of performing MMP measurements of any injected gas, liquid, or supercritical fluid as long as system components are capable of the required pressure and temperature conditions (and are not reactive with the injection fluid). For example, illustrations showing the capillary height versus injection pressure to determine MMP values for a crude oil with pure methane, representing natural gas, are set forth in FIG. 6 and set forth with pure nitrogen in FIG. 7. The apparatus used accommodates capillary tubes with three different inner diameters to yield triplicate verification of the MMP results from a single experiment as shown in FIGS. 1A, 1B, and 3.

As illustrated in FIG. 8, the effect of oil reservoir methane on the MMP values for injected carbon dioxide on the same sample of crude oil is set forth using the method and apparatus disclosed herein (e.g., a MMP determined using a fluid that is a $CO_2$/methane mixture). As shown in FIG. 8, the results show that increasing pressures of methane greatly increase the MMP of injected carbon dioxide. FIG. 8 illustrates forty eight (48) experimentally measured height-pressure correlations (including the triplicate data from each experiment) that were performed by a single analyst in a period of time less than one day.

Figure 9:
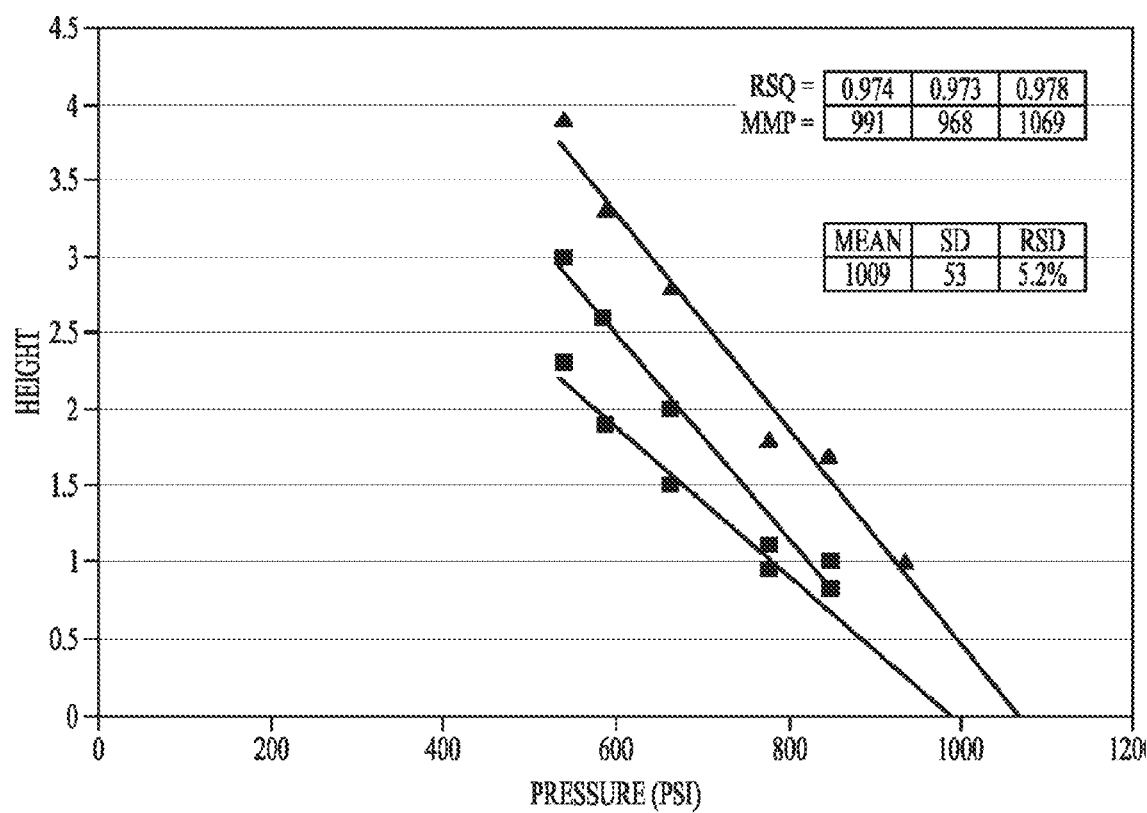
FIG. 9 illustrates MMP determination of $CO_2$ with crude oil after exposure to ethane, in accordance with various embodiments.

As illustrated in FIG. 9, the effect of ethane on the MMP values for injected carbon dioxide on the same sample of crude oil is set forth using the method and apparatus disclosed herein (e.g., a MMP determined using a fluid that is a $CO_2$/ethane mixture). As shown in FIG. 9, the results show that exposure to ethane at 540 psi prior to performing the MMP determination with carbon dioxide greatly decreases the MMP of injected carbon dioxide.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Additional Embodiments

The present invention provides for the following exemplary embodiments, the numbering of which is not to be construed as designating levels of importance:

Embodiment 1 provides a method of determining a minimum miscibility pressure of a fluid with an oil composition, the method comprising:

placing a fluid into a pressure chamber at a first pressure, the pressure chamber comprising at least one capillary tube having one end disposed in an oil composition in the pressure chamber, wherein the fluid comprises at least one of a gas, a liquid, and a supercritical fluid;

measuring a height of the oil composition in at least one of the capillary tubes;

repeating the measuring for at least one cycle using a second pressure different than the first pressure; and determining the minimum miscibility pressure of the oil composition with the fluid by extrapolating the pressure at a height of the oil in the at least one capillary tube of zero from the two or more measurements of the height of the oil composition in the at least one capillary tube.

Embodiment 2 provides the method of Embodiment 1, further comprising equilibrating pressure within the pressure chamber prior to measuring the height of the oil composition.

Embodiment 3 provides the method of any one of Embodiments 1-2, wherein the first pressure is about equal to a downhole pressure of crude oil in a subterranean formation.

Embodiment 4 provides the method of any one of Embodiments 1-3, wherein below the minimum miscibility pressure, the oil composition and the fluid form two phases separated by an interfacial tension between the phases.

Embodiment 5 provides the method of any one of Embodiments 1-4, wherein the second end of the capillary tubes is disposed in the fluid in the pressure chamber.

Embodiment 6 provides the method of any one of Embodiments 1-5, further comprising equilibrating temperature within the pressure chamber prior to measuring the height of the oil composition.

Embodiment 7 provides the method of any one of Embodiments 1-6, wherein a temperature within the pressure chamber is about equal to a downhole temperature of crude oil in a subterranean formation.

Embodiment 8 provides the method of any one of Embodiments 1-7, wherein the height of the oil composition in at least one of the capillary tubes is the distance between the surface of the oil composition in the pressure chamber and the surface of the oil composition in the capillary tube.

Embodiment 9 provides the method of any one of Embodiments 1-8, wherein for each cycle the second pressure is independently selected.

Embodiment 10 provides the method of any one of Embodiments 1-9, wherein for each cycle the second pressure is different.

Embodiment 11 provides the method of any one of Embodiments 1-10, wherein the first and second pressures are predetermined.

Embodiment 12 provides the method of any one of Embodiments 1-11, wherein the fluid comprises at least one of carbon dioxide, nitrogen, methane, ethane, propane, hydrogen sulfide, n-butane, iso-butane, natural gas, natural gas liquids, and produced gas.

Embodiment 13 provides the method of any one of Embodiments 1-12, wherein the oil composition comprises crude oil or a crude oil fraction.

Embodiment 14 provides the method of any one of Embodiments 1-13, wherein the oil composition comprises a live oil sample.

Embodiment 15 provides the method of any one of Embodiments 1-14, wherein the repeating of the measuring for at least one cycle using a second pressure different than the first pressure is performed in the same pressure cell or in a different pressure cell.

Embodiment 16 provides the method of any one of Embodiments 1-15, further comprising recording the measured height of the oil composition and the corresponding pressure at which the height was measured.

Embodiment 17 provides the method of any one of Embodiments 1-16, wherein the pressure chamber comprises at least two capillary tubes.

Embodiment 18 provides the method of Embodiment 17, wherein the measuring comprises measuring the height of the oil composition in each of the capillary tubes, wherein the determining the minimum miscibility pressure comprises extrapolating the pressure at a height of the oil in the at least one capillary tube of zero independently for each of the capillary tubes from the two or more measurements of the height of the oil composition in each of the capillary tubes.

Embodiment 19 provides the method of Embodiment 18, wherein the determining further comprises averaging the at least two extrapolated pressures.

Embodiment 20 provides the method of any one of Embodiments 17-19, wherein each capillary tube has a different diameter.

Embodiment 21 provides the method of any one of Embodiments 1-20, wherein at least one cycle is performed in a different pressure chamber.

Embodiment 22 provides the method of any one of Embodiments 1-21, wherein the oil composition comprises a plurality of compounds comprising at least one desired compound, further comprising selecting the first and second pressure such that each cause at least 5-99 wt % of the oil composition to become miscible with or substantially soluble in the fluid, such that the desired compound remains substantially immiscible with the fluid at the first and second pressure, such that the determined minimum miscibility pressure is approximately the minimum miscibility pressure of the fluid with the desired compound as measured with the desired compound in a substantially purified state.

Embodiment 23 provides the method of any one of Embodiments 1-22, wherein the oil composition comprises a plurality of compounds comprising at least one desired compound, further comprising selecting the first and second pressure such that each cause no more than 0-95 wt % of the oil composition to become miscible with or substantially soluble in the fluid, such that the desired compound remains substantially immiscible with the fluid at the first and second pressure, such that the determined minimum miscibility pressure is approximately the minimum miscibility pressure of the fluid with the desired compound as measured with the desired compound in a substantially purified state.

Embodiment 24 provides the method of any one of Embodiments 1-23, wherein the oil composition comprises a plurality of compounds each having a different molecular weight, wherein the method further comprises selecting a first and second pressure such that a majority of a desired molecular weight fraction the oil composition remains immiscible with the fluid, such that the determined minimum miscibility pressure is approximately the minimum miscibility pressure of the desired molecular weight fraction.

Embodiment 25 provides the method of any one of Embodiments 1-24, further comprising performing a flooding treatment of a subterranean formation comprising therein a petroleum composition that is the same as or substantially resembles the oil composition, wherein the flooding treatment is performed using the fluid at a pressure that is equal to or above the determined minimum miscibility pressure.

Embodiment 26 provides the method of Embodiment 25, further comprising performing the method of determining the minimum miscibility pressure using as the oil composition a sample produced from the subterranean formation after the flooding treatment has begun.

Embodiment 27 provides a method of flooding a subterranean formation with a fluid, the method comprising:

obtaining or providing a maximum pressure for a subterranean formation;

performing the method of any one of Embodiments 1-26 using as the oil composition a sample from the subterranean formation or that substantially resembles a sample from the subterranean formation;

adjusting the composition of the fluid and repeating the performance of the method, until at least one fluid composition is determined that has a lower minimum miscibility pressure with the oil composition than the maximum pressure for the subterranean formation; and performing a flooding treatment of the subterranean formation using the fluid at a pressure that is equal to or above the determined minimum miscibility pressure and below the maximum pressure for the subterranean formation.

Embodiment 28 provides a method of determining a minimum miscibility pressure of a fluid with an oil composition, the method comprising:

placing a fluid into a pressure chamber at a first pressure, the pressure chamber comprising a plurality of capillary tubes each having one end disposed in an oil composition in the pressure chamber and each having a different inner diameter, wherein the fluid comprises at least one of a gas, a liquid, and a supercritical fluid comprising at least one of carbon dioxide, nitrogen, methane, ethane, propane, hydrogen sulfide, n-butane, iso-butane, natural gas, natural gas liquids, and produced gas, wherein the oil composition comprises at least one of crude oil, a crude oil fraction, a mixture substantially resembling crude oil, and a mixture substantially resembling a crude oil fraction;

measuring a height of the oil composition in each of the capillary tubes;

repeating the measuring for at least one cycle using a second pressure different than the first pressure; and determining the minimum miscibility pressure of the oil composition with the fluid by extrapolating the pressure at a height of the oil in the at least one capillary tube of zero independently for each of the capillary tubes from the two or more measurements of the height of the oil composition in each of the capillary tubes, and averaging the at least two extrapolated pressures.

Embodiment 29 provides an apparatus for determining a minimum miscibility pressure of a fluid with an oil composition, the apparatus comprising:

a pressure chamber comprising at least one capillary tube configured to have one end disposed in an oil composition therein, the pressure chamber configured to have a fluid comprising at least one of a gas, a liquid, and a supercritical fluid placed therein at a first pressure;

wherein the pressure chamber is configured such that a height of the oil composition in at least one of the capillary tubes can be measured.

Embodiment 30 provides the apparatus of Embodiment 29, wherein the pressure chamber is configured to have the fluid placed therein at the first pressure and at a second pressure, wherein the pressure chamber is configured such that the height of the oil composition in at least one of the capillary tubes can be measured, such that the minimum miscibility pressure of the oil composition with the fluid can be determined by extrapolating the pressure at a height of the oil in the at least one capillary tube of zero from the two or more measurements of the height of the oil composition in the at least one capillary tube.

Embodiment 31 provides the apparatus of any one of Embodiments 29-30, wherein the pressure chamber comprises at least two capillary tubes each having a different inner diameter.

Embodiment 32 provides the apparatus of any one of Embodiments 29-31, wherein the apparatus further comprises a holder for the at least one capillary tube.

Embodiment 33 provides the apparatus of any one of Embodiments 29-32, further comprising a recorder that is configured to record a pressure of the fluid and the corresponding height of the oil composition in at least one of the capillary tubes.

Embodiment 34 provides a method of sampling one or more components of an oil composition, the method comprising:

placing a fluid into a pressure chamber at a first pressure, the pressure chamber comprising an oil composition therein sufficient to contact the fluid, wherein the fluid comprises at least one of a gas, a liquid, and a supercritical fluid; and taking a sample of at least one of the fluid and the oil composition from the pressure chamber.

Embodiment 35 provides the method of Embodiment 34, further comprising characterizing at least one aspect of the sample.

Embodiment 36 provides an apparatus for sampling at least one component of an oil composition, the apparatus comprising:

a pressure chamber configured to have oil composition therein, the pressure chamber configured to have a fluid comprising at least one of a gas, a liquid, and a supercritical fluid placed therein at a first pressure sufficient to contact the oil composition;

wherein the pressure chamber is configured such that a sample of at least one of the fluid and the oil composition can be taken at the first pressure.

Embodiment 37 provides the apparatus or method of any one or any combination of Embodiments 1-36 optionally configured such that all elements or options recited are available to use or select from.

What is claimed is:

1. A method of determining a minimum miscibility pressure of a fluid with an oil composition, the method comprising:

placing a fluid into a pressure chamber at a first pressure, the pressure chamber comprising a plurality of capillary tubes each having one end disposed in an oil composition in the pressure chamber and with each of the capillary tubes having a different diameter, wherein the fluid comprises at least one of a gas, a liquid, and a supercritical fluid, wherein the oil composition comprises a plurality of compounds each having a different molecular weight;

measuring a height of the oil composition in each of the capillary tubes;

repeating the measuring for at least one cycle using a second pressure different than the first pressure, wherein the first and second pressure are selected such that a majority of a desired molecular weight fraction of the oil composition remains immiscible with the fluid; and determining the minimum miscibility pressure of the desired molecular weight fraction of the oil composition with the fluid by extrapolating the pressure at a height of a fluid-fluid interface between the desired molecular weight fraction and the fluid in the capillary tubes of zero independently for each of the capillary tubes from the two or more measurements of the height of the fluid-fluid interface between the desired molecular weight fraction and the fluid in each of the capillary tubes and averaging the at least two extrapolated pressures.

2. The method of claim 1, further comprising equilibrating pressure within the pressure chamber prior to measuring the height of the fluid-fluid interface between the desired molecular weight fraction and the fluid.

3. The method of claim 1, wherein the second end of the capillary tubes is disposed in the fluid in the pressure chamber.

4. The method of claim 1, further comprising equilibrating temperature within the pressure chamber prior to measuring the height of the fluid-fluid interface between the desired molecular weight fraction and the fluid.

5. The method of claim 1, wherein the height of the fluid-fluid interface between the desired molecular weight fraction and the fluid in at least one of the capillary tubes is the distance between the surface of the oil composition in the pressure chamber and the surface of the fluid-fluid interface between the desired molecular weight fraction and the fluid in the capillary tube.

6. The method of claim 1, wherein the fluid comprises at least one of carbon dioxide, nitrogen, methane, ethane, propane, hydrogen sulfide, n-butane, iso-butane, natural gas, natural gas liquids, and produced gas.

7. The method of claim 1, wherein the oil composition comprises crude oil or a crude oil fraction.

8. The method of claim 1, wherein the oil composition comprises a live oil sample.

9. The method of claim 1, wherein the oil composition comprises a plurality of compounds comprising at least one desired compound, further comprising selecting the first and second pressure such that each cause at least 5-99 wt % of the oil composition to become miscible with or substantially soluble in the fluid, such that the desired compound remains substantially immiscible with the fluid at the first and second pressure, such that the determined minimum miscibility pressure is approximately the minimum miscibility pressure of the fluid with the desired compound.

10. The method of claim 1, wherein the oil composition comprises a plurality of compounds comprising at least one desired compound, further comprising selecting the first and second pressure such that each cause no more than 0-95 wt % of the oil composition to become miscible with or substantially soluble in the fluid, such that the desired compound remains substantially immiscible with the fluid at the first and second pressure, such that the determined minimum miscibility pressure is approximately the minimum miscibility pressure of the fluid with the desired compound.

11. The method of claim 1, further comprising performing a flooding treatment of a subterranean formation comprising therein a petroleum composition that is the same as or substantially resembles the oil composition, wherein the flooding treatment is performed using the fluid at a pressure that is equal to or above the determined minimum miscibility pressure.

12. The method of claim 11, further comprising performing the method of determining the minimum miscibility pressure using as the oil composition a sample produced from the subterranean formation after the flooding treatment has begun.

13. A method of flooding a subterranean formation with a fluid, the method comprising:

obtaining or providing a maximum pressure for a subterranean formation;
performing the method of claim 1 using as the oil composition a sample from the subterranean formation or that substantially resembles a sample from the subterranean formation;
adjusting the composition of the fluid and repeating the performance of the method, until at least one fluid composition is determined that has a lower minimum miscibility pressure with the oil composition than the maximum pressure for the subterranean formation; and
performing a flooding treatment of the subterranean formation using the fluid at a pressure that is equal to or above the determined minimum miscibility pressure and below the maximum pressure for the subterranean formation.

14. A method of determining a minimum miscibility pressure of a fluid with an oil composition, the method comprising:
placing a fluid into a pressure chamber at a first pressure, the pressure chamber comprising a plurality of capillary tubes each having one end disposed in an oil composition in the pressure chamber and with each of the capillary tubes having a different diameter, wherein the fluid comprises at least one of a gas, a liquid, and a supercritical fluid, wherein the oil composition comprises one or more desired compounds;
measuring a height of the oil composition in each of the capillary tubes;
repeating the measuring for at least one cycle using a second pressure different than the first pressure, wherein the first and second pressure are selected such that each cause at least about 5 wt % to about 99 wt % of the oil composition to become miscible with or substantially soluble in the fluid, such that the one or more desired compounds remain substantially immiscible with the fluid at the first and second pressure; and
determining the minimum miscibility pressure of the one or more desired compounds with the fluid by extrapolating the pressure at a fluid-fluid interface between the one or more desired compounds and the fluid in the capillary tubes of zero independently for each of the capillary tubes from the two or more measurements of the height of fluid-fluid interface between the one or more desired compounds and the fluid in each of the capillary tubes and averaging the at least two extrapolated pressures.

15. A method of determining a minimum miscibility pressure of a fluid with an oil composition, the method comprising:
placing a fluid into a pressure chamber at a first pressure, the pressure chamber comprising a plurality of capillary tubes each having one end disposed in an oil composition in the pressure chamber and with each of the capillary tubes having a different diameter, wherein the fluid comprises at least one of a gas, a liquid, and a supercritical fluid, wherein the oil composition comprises one or more desired compounds;
measuring a height of the oil composition in each of the capillary tubes;
repeating the measuring for at least one cycle using a second pressure different than the first pressure, wherein the first and second pressure are selected such that each cause no more than about 0 wt % to about 95 wt % of the oil composition to become miscible with or substantially soluble in the fluid, such that the one or more desired compounds remain substantially immiscible with the fluid at the first and second pressure; and
determining the minimum miscibility pressure of the one or more desired compounds of the oil composition with the fluid by extrapolating the pressure at a height of a fluid-fluid interface between the one or more desired compounds and the fluid in the capillary tubes of zero independently for each of the capillary tubes from the two or more measurements of the height of the fluid-fluid interface between the one or more desired compounds and the fluid in each of the capillary tubes and averaging the at least two extrapolated pressures.

* * * * *